United States Patent [19]

Krol

[11] Patent Number: 4,573,576

[45] Date of Patent: Mar. 4, 1986

[54] PERCUTANEOUS GASTROSTOMY KIT

[76] Inventor: Thomas C. Krol, 3344 Ironwood Dr., Oceanside, Calif. 92056

[21] Appl. No.: 545,827

[22] Filed: Oct. 27, 1983

[51] Int. Cl.⁴ .................. B65D 85/54; A61M 21/00
[52] U.S. Cl. .................................. 206/471; 206/571; 206/366; 206/438; 604/29; 604/104; 604/280
[58] Field of Search ............. 206/471, 366, 369, 438, 206/439, 63.3, 571; 604/29, 104, 105, 280, 281, 282

[56] References Cited

U.S. PATENT DOCUMENTS

| | | | |
|---|---|---|---|
| 504,424 | 9/1893 | Pezzer | 604/104 |
| 2,458,305 | 1/1949 | Sanders | 604/282 |
| 3,013,656 | 12/1961 | Murphy, Jr. | 206/571 |
| 3,042,044 | 7/1962 | Sheridan | 604/104 |
| 3,094,124 | 6/1963 | Birtwell | 604/280 |
| 3,256,981 | 6/1966 | Kurtz | 206/63.3 |
| 3,416,531 | 12/1968 | Edwards | 604/282 |
| 3,459,189 | 8/1969 | Alley et al. | 604/281 |
| 3,473,646 | 10/1969 | Burke | 206/471 |
| 3,589,368 | 6/1971 | Jackson et al. | 604/280 |
| 3,642,126 | 2/1972 | Kurtz et al. | 206/63.3 |
| 3,690,315 | 9/1972 | Chittenden et al. | 206/438 |
| 3,892,314 | 7/1975 | Semp | 206/63.3 |
| 3,930,580 | 1/1976 | Bazell et al. | 206/439 |
| 4,055,672 | 10/1977 | Hirsch et al. | 206/439 |
| 4,160,505 | 7/1979 | Rauschenberger | 206/571 |
| 4,351,333 | 9/1982 | Lazarus et al. | 604/29 |
| 4,411,655 | 10/1983 | Schreck | 604/281 |

FOREIGN PATENT DOCUMENTS 885054 12/1961 United Kingdom ............... 604/280

Primary Examiner—William T. Dixson, Jr.
Assistant Examiner—Brenda J. Ehrhardt
Attorney, Agent, or Firm—Baker, Maxham, Callan & Jester

[57] ABSTRACT

A percutaneous gastrostomy kit includes a mushroom catheter having a closed proximal end with a transverse bore through said end and an enlarged washer on the distal end adjacent the mushroom head, a length of approximately five feet of number 2 suture thread, a small packet of surgical lubricant, and a medicut catheter of about 16 gauge all sterilized and enclosed within a sealed package.

14 Claims, 7 Drawing Figures

PERCUTANEOUS GASTROSTOMY KIT

BACKGROUND OF THE INVENTION

The present invention relates to medical apparatus and pertains particularly to an improved percutaneous gastrostomy kit.

Many medical patients who have lost the ability to swallow may have an intact gut and require long-term nutritional support. The conventional approach to this problem has been to place a gastrostomy surgically or to leave a nasogastric tube in place for long periods.

A recent approach to this problem has been the placement of a gastrostomy tube endoscopically. This permits the placement of a gastrostomy tube through a much smaller opening in the walls of the stomach avoiding general anesthesia and the use of an operating room. This most recent approach is discussed in a publication entitled "Percutaneous Endoscopic Gastrostomy" by David E. Larson, M.D., et al., published by the Mayo Clinic, Proc 58: 103–107, 1983. This publication describes a procedure wherein the site of placement of gastrostomy is located by an endoscope with an opening made into the skin and abdominal wall by a scalpel blade and then a 16-gauge Medicut catheter introduced through the opening into the stomach and a silk suture passed through the catheter and grasped with a standard biopsy forceps with the suture and endoscope then removed from the patient in a conventional fashion. Thread from the mouth of the patient is then backfed through a first Medicut sheath and then through a second sheath which has been inserted through the proximal end of a modified 16-F Pezzer "mushroom" catheter. The second sheath is removed and discarded, the thread left in place and the Medicut sheath is then pulled over the catheter to protect the knot and serve as a dilator. The catheter is then lubricated and pulled through the mouth, esophagus, stomach, and finally, abdominal wall until only the rubber bumper and mushroom head remain in the stomach. A rubber bumper is specially prepared for the catheter by cutting a hole through an elastic tube and inserting the catheter through the hole such that the tube extends transverse to the axis of the catheter. This procedure requires the time consuming assembly and preparation of several separate components in preparation for the operation.

It is desirable that an improved kit be available having the necessary components with desirable modifications for simplifying and improving the gastrostomy procedures.

SUMMARY AND OBJECTS OF THE INVENTION

It is, therefore, the primary object of the present invention to provide an improved kit for percutaneous endoscopic gastrostomy.

In accordance with the primary aspect if the present invention, a percutaneous gastrostomy kit includes a modified mushroom catheter having a closed proximal end with a transverse bore for receiving a suture thread and at least one stop washer adjacent the head of the catheter, a length of approximately five feet of No. 2 silk suture thread, and Medicut catheter of about 16 gauge, all contained in a sealed container.

BRIEF DESCRIPTION OF THE DRAWINGS

The above and other objects and advantages of the present invention will become apparent from the following description when read in conjunction with the drawings wherein.

DETAILED DESCRIPTION OF A PREFERRED EMBODIMENT

Figure 1:
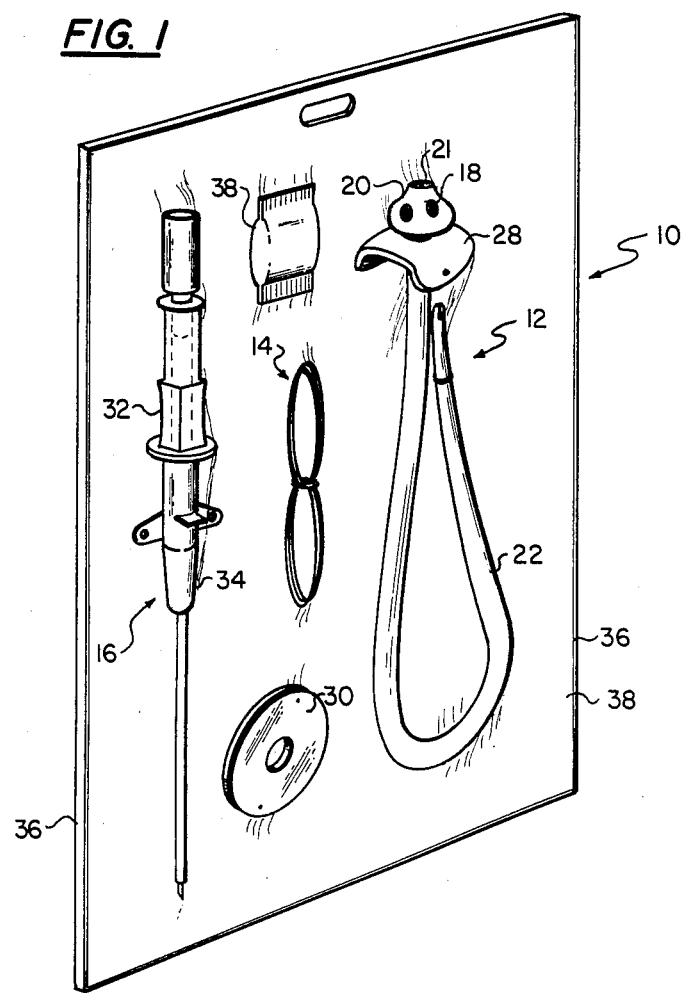
FIG. 1 is a perspective view of a preferred embodiment of the kit in accordance with the invention.
Figure 2:
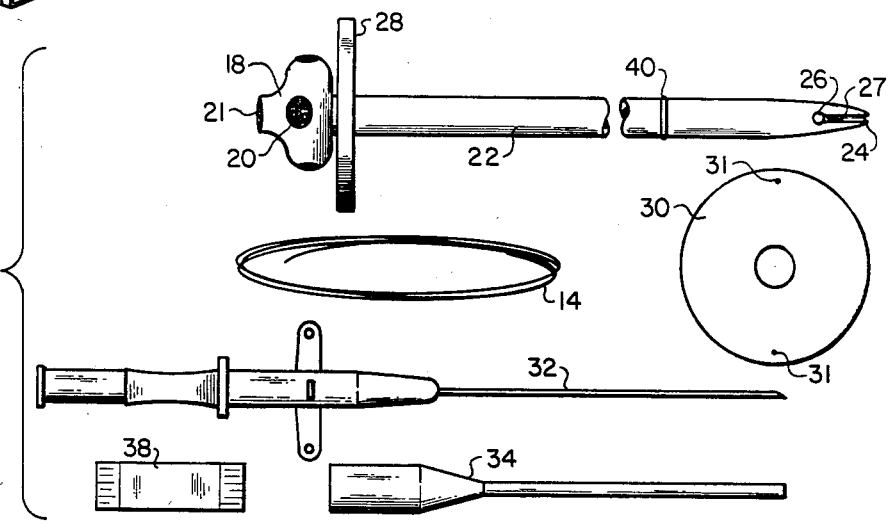
FIG. 2 is a plan view showing the separate elements of the components of the kit.

Referring to FIGS. 1 and 2 of the drawing, a kit in accordance with the invention designated generally by the numeral 10 includes a mushroom catheter designated generally by the numeral 12, a quantity of silk suture designated generally by the numeral 14, an outer washer 30, and a needle and Medicut catheter combination 16, all contained within a container in the form as illustrated of a bubble pack. A packet of surgical lube 38 is also preferably included but not essential.

Figure 4:
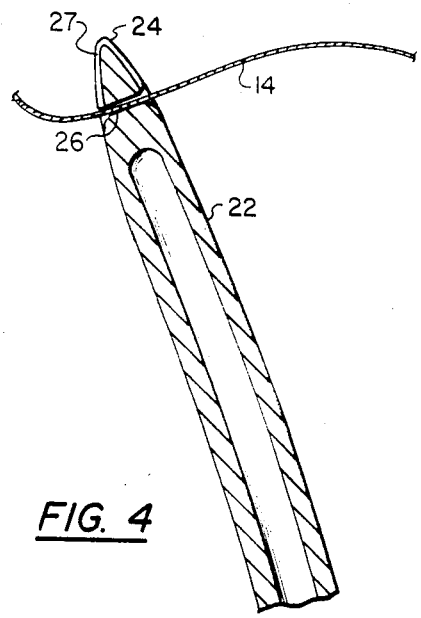
FIG. 4 is an enlarged detailed view showing details of the catheter of the invention.

The mushroom catheter is slightly modified from conventional construction but includes the conventional mushroom head 18 containing a plurality of ports 20, with an additional end port 21 aligned with the tube 22. This enables access through tube 22 and port 21 into the stomach with other tubes, etc. Flexible tube 22 of the mushroom catheter is a unitary structure therewith and has a proximal end 24 that is closed and tapered down to a small rounded point. The tapered and rounded proximal end serves as a dilator. A suture receiving transverse bore 26 extends through the catheter near the proximal end 24 which has been formed to be closed as shown in FIG. 4. This closed end with bore 26 provides a strong connective structure that enables the secure connection of a silk suture to the end of the catheter to draw it through the esophagus and stomach out through an opening in the stomach wall. A groove 27 for receiving the suture 14 and a knot therein extends across the end 24 of the tube from one end of eye or bore 26 to the other. This places the suture and knot within the groove below the surface of the tube.

The suture material 14 is preferably silk thread of a number 2 size (although nylon or other materials may be used) and having a length about five feet. This provides a suture that is sufficiently strong to draw the catheter into place. A first washer or stop 28 in the form of a rubber or resilient plastic disk 28 has a bore through the center thereof for receiving the catheter tube 22. This washer 28 also serves as a stop and seal for sealing around the opening in the stomach and to stop the catheter head 18 from pulling through the stomach opening. Another washer 30 having suture holes 31 is provided for fitting around the opening and snugly around the catheter tube outside the stomach for sealing and securing the catheter to the skin.

An I.V. needle and Medicut catheter or sheath is also included in the kit and is utilized as will be explained for placement of the suture through the opening into the stomach to be grasped by forceps to be pulled through the stomach and out the mouth. The needle assembling was a needle 32 which is normally covered as shown in FIG. 1 by a sheath or Medicut catheter 34. This kit provides the necessary components for the endoscopic placement of a permanent feeding gastrostomy.

Figure 3:
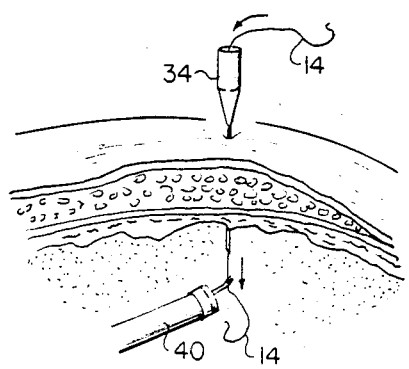
FIG. 3 is an enlarged partial view in section showing a step in the procedure of utilizing the invention.
Figure 5:
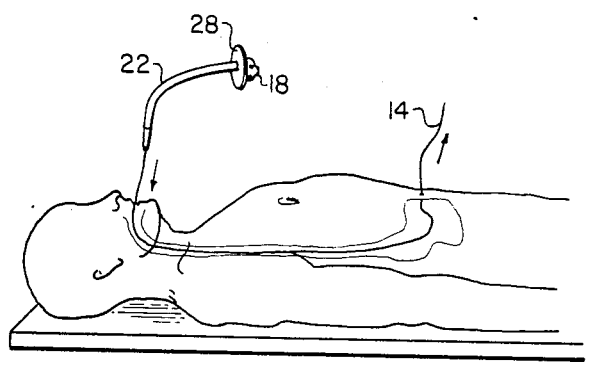
FIG. 5 is a side elevation view illustrating the procedure of insertion of the catheter.

In use of the kit as illustrated in FIGS. 3 through 7, a fiber-optic endoscope 42 is inserted through the esophagus into the stomach of the patient to a suitable position for the gastrostomy catheter. The position is located such as by locating the end of the optical tube and forming an opening through the skin and abdominal wall by means of a surgical knife or as by means of a needle unit 16 with the Medicut catheter 34 left in place. As shown in FIG. 3, the suture 14 is fed through the Medicut catheter 34 down into the stomach cavity and is grasped by forceps 44 on the end of the distal end of the endoscope 42. The suture material is grasped and the fiberscope withdrawn drawing the suture with it through the stomach, esophagus and out the mouth as shown in FIG. 5. The suture 14 then extends through the stomach opening through the stomach, esophagus and out the mouth and is attached as shown in FIG. 4 to the end of the mushroom-feeding catheter. The suture is threaded through the eye or transverse bore 26 in the end of the catheter as shown in FIG. 4.

Figure 6:
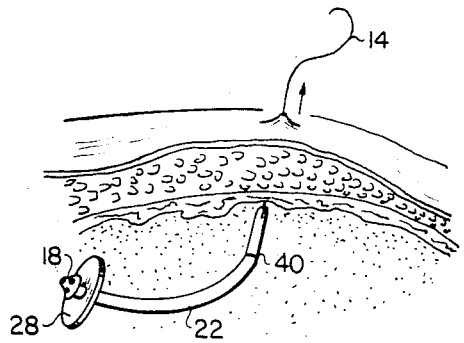
FIG. 6 is a view like FIG. 3 showing the catheter in place.
Figure 7:
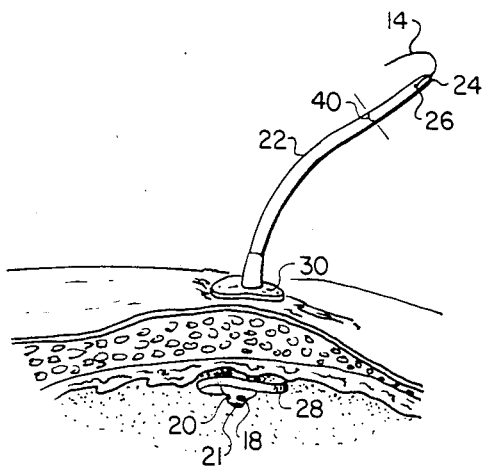

After the suture is attached in eye 25 and groove 25 to the end of the catheter, the end 24 of the catheter is lubricated, the opposite end of the suture is grasped in the hand and the catheter is pulled into the mouth, down the esophagus, through the stomach and out the opening as shown in FIGS. 6 and 7. The washer 28 in place on the catheter tube snugs against the inner stomach wall as the catheter tube is pulled in place. Thereafter, the outer washer or seal 30 is put into position on the outside over the catheter and outer opening through the stomach wall and sewn to the skin with suture through small holes 31 near the outer edge thereof. The outer end 24 of the catheter tube is then cut off at a position, preferably marked by a line 40, a sufficient distance from the end to open the tube. The catheter tube is then prepared and feeding can begin. The catheter tube 22 is preferably a size identifed as 20 French.

The kit is packaged in a suitable container and is preferably sterilized such as by gas sterilization or the like and prepackaged in a sterile sealed container. For the purposes of illustration, a bubble pack type of package or container is illustrated having a backing board or panel 36 such as cardboard with a seal sheet of transparent plastic or the like vacuum sealed over the components of the kit lying on the surface of the pack. Other forms of packaging may be utilized. This provides a readily available kit of the necessary components to perform the gastrostomy.

While I have illustrated and described my invention by means of specific embodiment, it is to be understood that numerous changes and modifications may be made therein without departing from the spirit and scope of the invention as defined in the appended claims.

I claim:

1. A gastrostomy kit, comprising:
   a mushroom catheter of a unitary construction having a closed proximal end and a transverse bore at said proximal end;
   a washer for placement on the catheter at the distal end adjacent the mushroom head;
   a length of approximately five feet of No. 2 suture thread; and
   a Medicut catheter of about 16 gauge.

2. The gastrostomy kit of claim 1 wherein the items recited in claim 1 are sterilized and disposed in a sealed container.

3. The gastrostomy kit of claim 2 including a second washer.

4. The gastrostomy kit of claim 3 wherein said suture thread is nylon.

5. The gastrostomy kit of claim 3 wherein said suture thread is silk.

6. A percutaneous gastrostomy kit comprising:
   a sealable container;
   a mushroom catheter of a unitary construction having an enlarged elastic disc adjacent the head and a tapered closed proximate end with a suture receiving transverse bore therethrough;
   an elongated quantity of about five feet of No. 2 suture thread; and
   a Medicut catheter of about 16 gauge.

7. A gastrostomy kit of claim 6 including a suture receiving groove across said proximal end connecting the ends of said transverse bore.

8. The gastrostomy kit of claim 6 wherein said mushroom catheter includes a mushroom-shaped head having at least one port aligned with the catheter tube.

9. The gastrostomy kit of claim 8 including an outer sealing washer.

10. The gastrostomy kit of claim 9 including a packet of surgical lube.

11. The gastrostomy kit of claim 1 wherein said mushroom catheter comprises a mushroom shaped head having at least one port aligned with the catheter tube.

12. The gastrostomy kit of claim 1 wherein said washer comprises an elastic disc having a bore smaller than the head of said mushroom catheter.

13. A percutaneous gastrostomy kit comprising:
    a sealable container;
    a mushroom catheter of a unitary construction comprising an elongated elastic tube having a mushroom shaped head on one end thereof with a plurality of ports in said head, including one port aligned with the bore of said tube, said tube having a closed other end and a suture receiving transverse bore through said closed other end;
    a quantity of about five feet of elongated No. 2 suture thread;
    an inner sealing elastic washer for inserting on said tube adjacent said head;
    an outer sealing elastic washer for extending over said tube;
    a Medicut catheter of about 16 gauge; and
    a packet of surgical lube;

14. A cathether for percutaneous gastrostomy comprising:
    a mushroom catheter of a unitary construction comprising an elongated elastic tube having a distal end and a proximal end;
    a hollow mushroom shaped head on the distal end of said elastic tube, said head having a plurality of ports formed in said head, one of said ports being aligned with the bore of said tube; said proximal end of said tube being closed and tapered downward from the tube diameter to a generally rounded point smaller in diameter than the tube and defining a dialator; and, a suture receiving transverse bore through said closed proximal end.

* * * * *